US012558441B2

(12) United States Patent
Droeschel

(10) Patent No.: US 12,558,441 B2
(45) Date of Patent: Feb. 24, 2026

(54) DEVICE AND METHOD FOR STERILIZING AND DRYING MEDICAL FILTERS

(71) Applicant: Allmed Dialysis Technologies GmbH, Pulsnitz (DE)

(72) Inventor: Stefan Droeschel, Wadern (DE)

(73) Assignee: Allmed Dialysis Technologies GmbH, Pulsnitz (DE)

( * ) Notice: Subject to any disclaimer, the term of this patent is extended or adjusted under 35 U.S.C. 154(b) by 432 days.

(21) Appl. No.: 18/033,095

(22) PCT Filed: Oct. 22, 2021

(86) PCT No.: PCT/DE2021/100851
§ 371 (c)(1),
(2) Date: Apr. 21, 2023

(87) PCT Pub. No.: WO2022/089685
PCT Pub. Date: May 5, 2022

(65) Prior Publication Data
US 2023/0390432 A1 Dec. 7, 2023

(30) Foreign Application Priority Data
Oct. 26, 2020 (DE) ..................... 10 2020 128 083.1

(51) Int. Cl.
*A61L 2/00* (2006.01)
*A61L 2/07* (2006.01)
(Continued)

(52) U.S. Cl.
CPC ................... *A61L 2/07* (2013.01); *A61L 2/26* (2013.01); *A61L 2103/15* (2026.01); *A61L 2202/122* (2013.01); *A61L 2202/123* (2013.01)

(58) Field of Classification Search
CPC ... C02F 1/00; B01D 41/04; A61L 2/07; A61L 2/26; A61L 2202/122
(Continued)

(56) References Cited

U.S. PATENT DOCUMENTS 4,195,061 A 3/1980 Kalasek
4,609,728 A 9/1986 Spranger et al.
(Continued)

FOREIGN PATENT DOCUMENTS

AT 351 172 B 7/1979
CN 111167778 A 5/2020
DE 11 2005 002 948 T5 1/2008

OTHER PUBLICATIONS

International Search Report in PCT/DE2021/100851, mailed Feb. 4, 2022.
(Continued)

*Primary Examiner* — Monzer R Chorbaji
(74) *Attorney, Agent, or Firm* — Collard & Roe, P.C.

(57) ABSTRACT

A device for sterilizing and drying filters, in particular medical filters such as dialyzers, includes a pressure chamber with at least one inlet and one outlet and a holder for at least one filter, as well as a method that sterilizes and dries filters. The pressure chamber is divided into a first chamber and a second chamber, wherein the filter is insertable into the holder such that the inlet port(s) of the filter are arranged in the first chamber and the outlet port(s) of the filter are arranged in the second chamber.

16 Claims, 1 Drawing Sheet

(51) Int. Cl.
| | |
|---|---|
| *A61L 2/08* | (2026.01) |
| *A61L 2/26* | (2006.01) |
| *B01D 21/00* | (2006.01) |
| *B01D 53/02* | (2006.01) |
| *A61L 103/15* | (2026.01) |

(58) Field of Classification Search
USPC ............ 422/24, 26; 55/96; 96/138; 210/303, 210/741, 771
See application file for complete search history.

(56) References Cited

U.S. PATENT DOCUMENTS

| | | | | |
|---|---|---|---|---|
| 5,840,343 | A * | 11/1998 | Hall, II .................... | A61L 2/186 |
| | | | | 422/12 |
| 5,945,006 | A * | 8/1999 | Mignani .............. | B01D 29/114 |
| | | | | 210/411 |
| 6,451,091 | B1 * | 9/2002 | Avina ..................... | B01D 46/44 |
| | | | | 96/138 |
| 6,663,814 | B2 * | 12/2003 | Kondou ................... | B01J 20/30 |
| | | | | 264/109 |
| 9,555,146 | B2 | 1/2017 | Fehr et al. | |
| 2003/0074862 | A1 | 4/2003 | Lohmuller | |
| 2011/0176959 | A1 | 7/2011 | Ko | |

OTHER PUBLICATIONS

International Preliminary Report on Patentability and English translation of Written Opinion of the International Searching Authority in PCT/DE2021/100851, dated May 2, 2023.

* cited by examiner

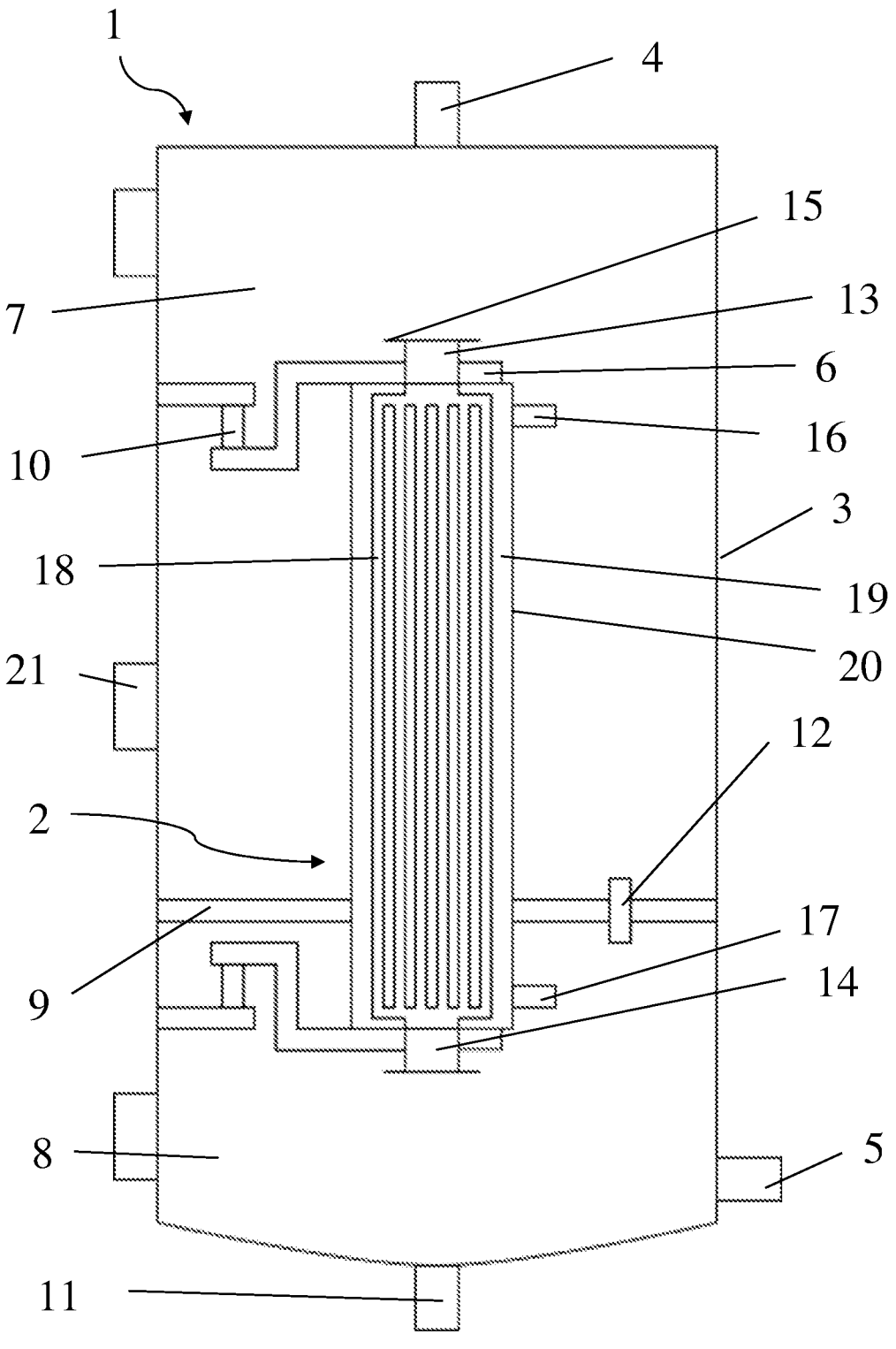

DEVICE AND METHOD FOR STERILIZING AND DRYING MEDICAL FILTERS

CROSS REFERENCE TO RELATED APPLICATIONS

This application is the National Stage of PCT/DE2021/100851 filed on Oct. 22, 2021, which claims priority under 35 U.S.C. § 119 of German Application No. 10 2020 128 083.1 filed on Oct. 26, 2020, the disclosure of which is incorporated by reference. The international application under PCT article 21(2) was not published in English.

The invention relates to a device for sterilizing and drying medical filters such as dialyzers, wherein the device comprises a pressure chamber having at least one inlet and one outlet and a holder for at least one filter, and to a method for sterilizing and drying filters.

Medical filters according to the present invention include, in particular, dialyzers, in particular hollow fiber dialyzers, in which the hollow fibers through which the blood flows form the filter membrane. These are used in hemodialysis. They consist of at least one hollow fiber module through which blood can be passed from a blood inlet opening to a blood outlet opening. The blood inlet opening and the blood outlet opening delimit a blood space. The dialyzers also have an inlet opening and an outlet opening for the dialysis fluid. The dialysis fluid flows around the hollow fibers, wherein the substances to be filtered from the blood pass through the hollow fiber membrane from the blood into the dialysis fluid.

Due to the direct blood contact of the dialyzer's blood chamber with the patient's blood, it must be sterile.

Sterilization processes for dialyzers are based, for example, on the use or application of gamma radiation, electron radiation, ethylene oxide (EtO) and superheated steam. In these processes, radiation, heat and toxicity are the effects that kill microorganisms.

In medical technology, autoclaves are used for the superheated steam sterilization of medical articles. Sterilization is achieved by displacing the air, applying superheated steam for a certain time, and a subsequent drying process. Sterilization kills germs and microorganisms that are hazardous to health. When sterilizing dialyzers in autoclaves, it has proved disadvantageous that drying the hydrophilic hollow fibers after hot steam sterilization is difficult and time-consuming.

A sterilization system for infusion solutions or the like filled into containers is known from AT 351 172, the housing of which comprises a heating chamber, a sterilization chamber and a cooling chamber.

DE 11 2005 002 948 T5 describes a hydrogen peroxide steam sterilizer and a sterilization method for using the same.

US 2003/0074862 A1 describes a method for steam sterilization of medical products, wherein the medical products are packed separately or in multiples in a carton, which is sealed, and then the medical products in the sealed carton are subjected to steam sterilization.

U.S. Pat. No. 4,609,728 A describes a method for treating a hollow cellulose fiber, which is particularly suitable for hemodialysis or other blood treatment outside the body.

U.S. Pat. No. 9,555,146 B2 discloses a method of sterilizing an object which comprises at least a first and a second opening to an interior of the object, comprising connecting the first opening to a supply line for a sterilant, connecting the second opening to an outlet line for the sterilant, and directing the sterilant through the supply line into the interior, through the interior, and out of the interior through the outlet line.

The object underlying the invention is that of optimizing the sterilization and drying of filters, in particular medical filters.

The object is achieved in a device according to one aspect of the invention in that the pressure chamber is divided into a first chamber and a second chamber, wherein the filter can be inserted into the holder in such a way that the inlet opening(s) of the filter are arranged in the first chamber and the outlet opening(s) of the filter are arranged in the second chamber.

The first and second chambers can be pressurized to between 0 and 10 bar.

Advantageously, the filter, which may be a dialyzer, can be inserted into the holder of the device. In this case, the blood inlet opening and the inlet opening for the dialysis fluid are arranged in the first chamber and the blood outlet opening and the outlet opening for the dialysis fluid are arranged in the second chamber. The same applies to other filters or medical filters. Residual air can be evacuated through the inlet of the chambers, and hot steam or dry air can be added. If both chambers are operated simultaneously, sterilization is also possible, e.g. using a vacuum/steam method.

Advantageously, however, superheated steam can also be introduced into the first chamber through the inlet for steam sterilization. This generates an overpressure in the first chamber. A pressure gradient is created between the first chamber and the second chamber. Here, the pressure difference can be small, to allow steam to flow slowly through the filter. For example, the pressure difference can be 100 mbar at a steam temperature of 123° C. Due to the pressure difference between the two chambers, superheated steam flows through the blood and dialysate space of the dialyzer from the blood inlet/dialysate inlet port to the blood outlet/dialysate outlet port, first displacing the air present. Then, the dialyzer is sterilized by exposing it to superheated steam for a set time. After exiting through the blood outlet opening/dialysate outlet opening, the superheated steam can be discharged from the second chamber via the outlet. The same applies to other filters or medical filters. It is also possible to combine the vacuum steam process with a permanent steam flow through the medical filter. The temperature range in the steam sterilization can be between 100-180° C. The duration of steam sterilization can be, for example, between 5 and 180 min.

The filter can be dried by evacuating the two chambers several times simultaneously and then filling them with dry air.

Advantageously, warm air can be introduced through the inlet into the first chamber to dry the dialyzer after steam sterilization. This creates a pressure gradient between the first chamber and the second chamber. This causes the warm air to flow through the blood and dialysate space of the dialyzer, drying the hollow fibers. The moisture is absorbed by the warm air in the process. After exiting through the blood outlet opening/dialysate outlet opening, the warm air can be discharged from the second chamber via the outlet. Particularly advantageously, this allows the dialyzer to be dried in less than half an hour, particularly advantageously in 20 minutes. The same applies to other filters or medical filters. The device can be operated in both horizontal and vertical orientation.

It is convenient that the pressure chamber is divided into a first chamber and a second chamber by a partition.

It is advantageously provided that the position of the partition can be adjusted.

The adjustable partition allows the size of the first chamber and the second chamber to be varied.

One embodiment of the invention is that the first chamber is larger than the second chamber.

Particularly advantageously, a larger area of the dialyzer can be arranged in the first chamber. In this case, the dialyzer can also be heated from the outside of the dialyzer as the steam flows in, thus promoting the sterilization. Drying can also be accelerated by flowing warm air into the first chamber, which can also heat the outside of the filter and thus accelerate the drying process. The same applies to other filters or medical filters.

A further embodiment of the invention consists in that means for applying a force to a filter located in the holder are provided in the region of the holder.

In particular, dialyzers with housings made of polypropylene expand during steam sterilization. By applying a force to the dialyzers during steam sterilization, the expansion of the dialyzers can be limited. In this case, the expansion of the dialyzers can be limited to less than 5 mm, preferably less than 2 mm, particularly preferably less than 1 mm. Advantageously, this preserves the ondulation of the hollow fiber bundles during steam sterilization. The force application can be adjusted depending on the dialyzer to be sterilized and the ondulation of the hollow fibers.

An advantageous embodiment of the invention is that a spring element or a pressure cylinder is provided for applying the force to a filter located in the holder.

The spring element or pressure cylinder makes it particularly easy to apply the force to the filter.

Another embodiment of the invention consists in that the device comprises a drain for condensed water in the bottom of each of the first chamber and the second chamber.

Advantageously, condensed steam can be led out of the pressure chamber via the drain. For example, condensate separators can be provided in both chambers.

Another embodiment of the invention consists in that the first chamber and the second chamber are interconnected by a valve.

When introducing steam for steam sterilization, the first chamber and the second chamber can be connected via the open valve. The steam can thus be distributed throughout the entire pressure chamber and enter the filter through all openings. The valve can be closed, for example, when drying the filter to allow warm air to flow through the filter via the pressure difference between the first chamber and the second chamber.

It is useful that the housing of the pressure chamber can be heated.

Heating the housing of the pressure chamber advantageously prevents the steam from condensing on the housing wall during steam sterilization or reduces the amount of condensate.

Finally, it is within the scope of the invention that the device includes emitters for introducing radiant energy into the filters.

By introducing radiation energy into the filters, they can be dried more quickly. The radiation can be microwave radiation or infrared radiation, for example.

The object is also achieved by a method for sterilizing and drying filters, in particular medical filters, according to another aspect of the invention. The method has the following steps:

inserting the filter into the holder,
closing the pressure chamber of the device, cyclic evacuation and steam inlet to both chambers for initial air removal,
introducing hot air into the first chamber and flowing through the filter for a set time to remove residual air,
pressurizing both chambers with superheated steam for a specified time,
displacement of the superheated steam via the outlet in the first chamber and/or second chamber by flowing hot air into the first chamber and/or second chamber and flowing through the filter until it is completely dry.

The object is also achieved by a method comprising the following steps:

inserting the filter into the holder,
closing the pressure chamber of the device,
introducing superheated steam via the inlet to the first chamber and/or the second chamber to remove the air present in the filter,
flowing superheated steam through the filter for a set time,
removing the hot steam via the outlet in the second chamber by displacement with air,
introducing warm air into the first chamber and/or the second chamber and flowing it through the filter until it is completely dry.

The object is also achieved by a method comprising the following steps:

inserting the filter into the holder,
closing the pressure chamber of the device,
cyclic evacuation and steam inlet to both chambers for air removal,
pressurizing both chambers with superheated steam for a specified time,
displacement of the superheated steam via the outlet in the first chamber and/or second chamber by flowing hot air into the first chamber and/or second chamber,
inflow of warm air into the first chamber and/or the second chamber and flow through the filter until it is completely dry.

The three aforementioned methods are each carried out with a device according to the invention.

In a preferred embodiment of the method, the filter is a medical filter, in particular a dialyzer, and the blood chamber of the medical filter, in particular dialyzer, is sealed with a steam-permeable and microbe-impermeable film before the sterilization process. The hollow fibers of the medical filter, in particular dialyzer, are first flowed through by the superheated steam, then applied with it for a predetermined time, and subsequently flowed through by the warm air.

For example, a film made of Tyvek® from DuPont can be used as a film that is vapor-permeable and impermeable to pathogens, for example microbes. The vapor-permeable and microbe-impermeable film provides a pyro-tight seal for the blood chamber of the medical filter, in particular dialyzer. Particularly advantageously, the blood inlet opening and the blood outlet opening of the medical filter, in particular dialyzer, no longer need to be sterilely wrapped after sterilization in the device.

The vapor-permeable and microbe-impermeable film can be, for example, a 0.2 micrometer thick membrane made of pyrogen-proof film.

In the case of dialyzers, it is advisable that the inlet opening and the outlet opening for the dialysis fluid are closed during the sterilization.

Advantageously, this favors the flow through the blood space of the dialyzer. The inlet opening and the outlet opening for the dialysis fluid can be closed with a cap, for example.

Finally, it is within the scope of the invention that the filter is dried by energy input or by radiation.

In the following, an exemplary embodiment of the invention is explained in more detail with reference to drawings. Here, the filter is a dialyzer.

The FIGURE shows in

FIG. 1 a cross section of a device according to the invention with a dialyzer inserted.

FIG. 1 shows a schematic representation of an embodiment of the device 1 according to the invention with dialyzer 2 inserted. The device consists of a cylindrical pressure chamber 3 with at least one inlet 4 and one outlet 5. Steam or warm air can be introduced into the pressure chamber 3 via the inlet 4. Residual air can also be removed from the chambers using a vacuum pump. Steam or warm air can be discharged from the pressure chamber 3 through the outlet 5. The pressure chamber 3 is divided by an adjustable partition 9 into a first chamber 7 and a second chamber 8, which are arranged vertically one above the other. Due to the adjustability of the partition 9, the size of the first chamber 7 and the second chamber 8 can be varied. The first chamber 7 and the second chamber 8 are connected by a valve 12 in the partition 9. The pressure chamber 3 can be opened and closed by a closing device 21. A drain for condensed water 11 is located at the bottom of the device 1.

Inside the pressure chamber is a holder 6 for inserting the dialyzer 2 to be sterilized. The holder comprises a spring element 10 for applying a force to the dialyzer 2 to limit the expansion of the dialyzer housing 20 during steam sterilization and subsequent drying. The blood inlet port 13 or the blood outlet port 14 of the blood chamber of the dialyzer 2 are received in the center of the holder 6. The blood space of the dialyzer 2 is formed by hollow fibers 18. The dialysis space 19 of the dialyzer 2 is located between the inlet opening 16 and the outlet opening 17 for dialysis fluid. The blood inlet opening 13 and the blood outlet opening 14 of the blood space of the dialyzer, respectively, are closed by a vapor-permeable and microbe-impermeable film 15. Through the vapor-permeable and microbe-impermeable foil 15, steam and air, but no pathogens hazardous to health, can penetrate into the blood chamber of the dialyzer.

To sterilize the dialyzer 2, the blood chamber of the dialyzer 2 is first sealed with a vapor-permeable and microbe-impermeable film 15, for example Tyvek® from DuPont. For this purpose, a vapor-permeable and microbe-impermeable film 15 is applied over each of the blood inlet opening 13 and blood outlet opening 14, for example by thermal welding. In the next step, the dialyzer 2 is placed in the holder 6 and the pressure chamber 3 of the device 1 is closed. Steam is then introduced into the first chamber 7 via the inlet 4. A pressure gradient between the first chamber 7 and the second chamber 8 causes steam to flow through the hollow fibers of the dialyzer 2 and remove the air therein. Subsequently, the dialyzer 2 is flowed through with superheated steam for a fixed time, for example 15 min, and thereby sterilized. The superheated steam is discharged from the pressure chamber 3 via the outlet 5 in the second chamber 8. To dry the dialyzer, warm air is introduced into the first chamber 7 via the inlet 4. A pressure gradient between the first chamber 7 and the second chamber 8 causes the warm air to flow through the hollow fibers of the dialyzer 2, with the moisture being absorbed by the warm air. The warm air is removed from the pressure chamber 3 via the outlet 5 in the second chamber 8.

The invention claimed is:

1. A device (1) for sterilizing and drying medical filters, wherein the device (1) comprises a pressure chamber (3)

with at least one inlet (4) and one outlet (5) and a holder (6) for at least one filter (2), wherein the pressure chamber is divided into a first chamber (7) and a second chamber (8) by a partition, wherein the filter (2) is insertable into the holder in such a way that the inlet opening(s) (13, 16) of the filter (2) are arranged in the first chamber (7) and the outlet opening(s) (14, 17) of the filter (2) are arranged in the second chamber (8).

2. The device (1) according to claim 1, wherein the position of the partition (9) is adjustable.

3. The device (1) according to claim 1, wherein the first chamber (7) is larger than the second chamber (8).

4. The device (1) according to claim 1, wherein means for applying a force to a filter (2) located in the holder are provided in the region of the holder (6).

5. The device (1) according to claim 4, wherein a spring element (10) or a pressure cylinder is provided for applying the force to a filter located in the holder (6).

6. The device (1) according to claim 1, wherein the device (1) comprises a drain for condensed water (11) in the bottom of the first chamber (7) and the second chamber (8), respectively.

7. The device (1) according to claim 1, wherein the first chamber (7) and the second chamber (8) are interconnected by a valve (12).

8. The device (1) according to claim 1, wherein the housing of the pressure chamber (3) is heatable.

9. The device (1) according to claim 1, wherein the device (1) comprises emitters for introducing radiant energy into the filters.

10. The device (1) according to claim 1, wherein the first chamber (7) and the second chamber (8) are pressurized to between 0 and 10 bar.

11. A method for sterilizing and drying filters (2) comprising the following steps:

> providing a device for sterilizing and drying the filters comprising a pressure chamber (3) with at least one inlet (4) and one outlet (5) and a holder (6) for at least one filter (2), wherein the pressure chamber is divided into a first chamber (7) and a second chamber (8) by a partition, wherein the filter (2) is insertable into the holder in such a way that the inlet opening(s) (13, 16) of the filter (2) are arranged in the first chamber (7) and the outlet opening(s) (14, 17) of the filter (2) are arranged in the second chamber (8),
>
> inserting the filter (2) into the holder (6),
>
> closing the pressure chamber (3) of the device (1),
>
> cyclic evacuation and steam inlet into both chambers for initial air removal,
>
> introducing hot air into the first chamber (7) and flowing through the filter (2) for a set time to remove residual air,
>
> pressurizing both chambers with superheated steam for a specified time,
>
> displacing the superheated steam via the outlet (5) in the first chamber (7) and/or second chamber (8) by flowing warm air into the first chamber (7) and/or second chamber (8) and flowing through the filter (2) until it is completely dry.

12. The method of claim 11, further comprising the steps of:

> inserting the filter (2) into the holder (6)
>
> closing the pressure chamber (3) of the device (1),
>
> introducing superheated steam via the inlet (4) into the first chamber (7) and/or the second chamber (8) to remove the air present in the filter (2), flowing superheated steam through the filter (2) for a specified time, removing the superheated steam via the outlet (5) in the second chamber (8) by displacement with air, introducing warm air into the first chamber (7) and/or the second chamber (8) and flowing through the filter until it is completely dry.

13. The method of claim 11, further comprising the following steps:

inserting the filter (2) into the holder (6), closing the pressure chamber (3) of the device (1), cyclic evacuation and steam inlet into both chambers for air removal, pressurizing both chambers with superheated steam for a specified time, displacing the superheated steam via the outlet (5) in the first chamber (7) and/or second chamber (8) by flowing warm air into the first chamber (7) and/or second chamber (8), inflow of warm air into the first chamber (7) and/or the second chamber (8) and flowing through the filter (2) until it is completely dry.

14. The method according to claim 11, wherein the filter (2) is a medical filter, and the blood space of the medical filter is sealed with a vapor-permeable and microbe-impermeable film before the introduction of superheated steam.

15. The method according to claim 11, wherein the filter (2) is dried by energy input or by radiation.

16. The method according to claim 11, wherein the first chamber (7) and the second chamber (8) are pressurized to between 0 and 10 bar.

* * * * *